United States Patent [19]

Giallorenzi

[11] Patent Number: 4,875,357
[45] Date of Patent: Oct. 24, 1989

[54] OPTICAL PARAMAGNETIC/DIAMAGNETIC GAS SENSOR

[75] Inventor: Thomas G. Giallorenzi, Springfield, Va.

[73] Assignee: United States of America as represented by the Secretary of the Navy, Washington, D.C.

[21] Appl. No.: 154,565

[22] Filed: Feb. 10, 1988

[51] Int. Cl.$^4$ ............... G01R 33/12; G01N 27/74
[52] U.S. Cl. ............................... 73/27 A; 324/204
[58] Field of Search ............... 73/27 A, 27, 23; 324/204

[56] References Cited

U.S. PATENT DOCUMENTS

| | | | |
|---|---|---|---|
| 3,487,297 | 12/1969 | Guyton | 73/27 A |
| 3,616,679 | 11/1969 | Meyer et al. | 73/27 A |
| 3,648,161 | 3/1972 | Cederstrand et al. | 324/204 |
| 3,742,344 | 6/1973 | Hummel | 73/27 A X |
| 3,815,018 | 6/1974 | Gast et al. | 73/27 A |
| 3,881,152 | 4/1975 | Tasaki | 73/27 A X |
| 4,403,186 | 9/1983 | Kotani et al. | 73/27 A |
| 4,563,894 | 1/1986 | Karrer | 73/27 A |

FOREIGN PATENT DOCUMENTS 225589  3/1943  Switzerland .................. 324/204

OTHER PUBLICATIONS

Publication, Introduction to Magnetic Materials, B. D. Cullity, Chapter 2, pp. 74–78 (1972).

Primary Examiner—Hezron E. Williams
Attorney, Agent, or Firm—Thomas E. McDonnell; George Jameson

[57] ABSTRACT

An improved gas sensor which optically senses a signal indication proportional to the concentration of a paramagnetic/diamagnetic gas in a gaseous mixture. In a preferred embodiment of the invention a chamber is adapted to contain a gaseous mixture to be measured for the concentration of a paramagnetic/diamagnetic gas in the mixture. An optical source provides light to a movable element coupled to the chamber. In response to the application of a magnetic field across the chamber, any paramagnetic/diamagnetic gas in the chamber causes the movable element to be displaced by a distance proportional to the concentration of the paramagnetic/diamagnetic gas in the gaseous mixture. A photodetector circuit receives light from the movable element having a characteristic indicative of the distance that the movable element was displaced. In response to such received light, the photodetector provides a signal output proportional to the concentration of the paramagnetic/diamagnetic gas in the gaseous mixture.

29 Claims, 4 Drawing Sheets

OPTICAL PARAMAGNETIC/DIAMAGNETIC GAS SENSOR

BACKGROUND OF THE INVENTION

The present application relates to gas sensors and particularly to a gas sensor which optically senses the concentration of a diamagnetic or paramagnetic gas in a gaseous mixture.

There are several commercial instruments on the market which measure the quantity of gas present by magnetic force methods. These techniques rely on the fact that when a paramagnetic or diamagnetic material is subjected to a magnetic field, these materials experience a force which is proportional to the applied magnetic field squared, i.e., $H^2$. The constant of proportionality is the product of the sample volume (number of molecules present) and magnetic susceptibility. Several experimental arrangements are currently employed which include the Faraday and the Gouy methods which are described in the book "Introduction to Magnetic Materials" by B. D. Cullity, Chapter 2, pp. 74–78 (1972). In general, these methods include measuring the force generated by the gas sample in the presence of the magnetic field and in some cases balancing out the force by a counter-applied force. Generally, electrical pickup techniques are used to measure the force. Once the force is measured, when the applied field is known, then the presence of a diamagnetic or paramagnetic gas may be determined if the susceptibility of the gas is known.

The force equation in its most general form is given by:

$$F = (K - K_o) a\, H^2/2,$$

where $K$ and $K_o$ are the susceptibilities of the material (gas) to be detected and of the background median, respectively, a is the cross-sectional area of the sample and H is the applied magnetic field. Because of the small size of the susceptibilities involved and electronic noise, the precision or accuracy of these measurements is limited. Furthermore, remote detection and/or analysis is limited because of the difficulty in performing high precision measurements electronically at any substantial distances. Electromagnetic pickup techniques severely limit the environments in which remote sensing is possible and are restricted to non-explosive and low electromagnetic interference (EMI) environments.

OBJECTS OF THE INVENTION

One object of the invention is to provide an improved oxygen sensor.

Another object of the invention is to provide an apparatus for sensing gases which have diamagnetic or paramagnetic properties.

Another object of the invention is to provide a fiber optical oxygen sensor.

Another object of the invention is to provide an optical gas sensor which determines the concentration of a paramagnetic/diamagnetic gas in a gaseous mixture by optically measuring the small displacement of a movable element produced by the application of a magnetic field to the gaseous mixture.

Another object of the invention is to provide a gas sensor which is capable of being passively and remotely activated and monitored to detect the presence of a paramagnetic or diamagnetic gas in a gaseous mixture.

Another object of the invention is to provide an interferometric optical fiber sensor for measuring the concentration of a paramagnetic/diamagnetic gas in a gaseous mixture.

Another object of the invention is to provide a fiber optic oxygen sensor that uses the paramagnetism of oxygen molecules to optically sense the concentration of oxygen in a gaseous mixture.

Another object of the invention is to provide a gas sensor which determines the concentration of a paramagnetic/diamagnetic gas in a gaseous mixture subjected to a magnetic field by optically sensing the phase shift induced by, for example, the stretching of an optical fiber or the movement of a reflective member as a function of the concentration of the paramagnetic/diamagnetic gas in the gaseous mixture.

A further object of the invention is to provide an improved oxygen sensor in which the application of a magnetic field to a gaseous mixture containing a paramagnetic/diamagnetic gas causes a deflection of an element which is optically sensed and photodetected to provide a signal amplitude proportional to the concentration of the paramagnetic/diamagnetic gas in the gaseous mixture.

SUMMARY OF THE INVENTION

These and other objects of this invention are achieved by providing an apparatus which comprises: a chamber adapted to contain a sample of a gaseous mixture to be measured for the amount of a paramagnetic or diamagnetic gas in the mixture; a movable element coupled to the chamber; optical source means for providing light to the movable element; magnetic means for developing a magnetic field across the chamber, the paramagnetic or diamagnetic gas in the chamber being responsive to the application of the magnetic field across the chamber for causing the movable element to be deflected a distance proportional to the concentration of paramagnetic or diamagnetic gas in the mixture; and photodetection means for receiving light from the movable element, the received light having a characteristic indicative of the distance that the movable element is deflected, the photodetection means being responsive to the received light for providing a signal amplitude proportional to the concentration of the paramagnetic or diamagnetic gas in the gaseous mixture.

BRIEF DESCRIPTION OF THE DRAWINGS

These and other objects, features and advantages of the invention, as well as the invention itself, will become better understood by reference to the following detailed description when considered in connection with the accompanying drawings wherein like reference numerals designate identical or corresponding parts throughout the several views, and wherein.

DETAILED DESCRIPTION OF THE INVENTION

Figure 1:
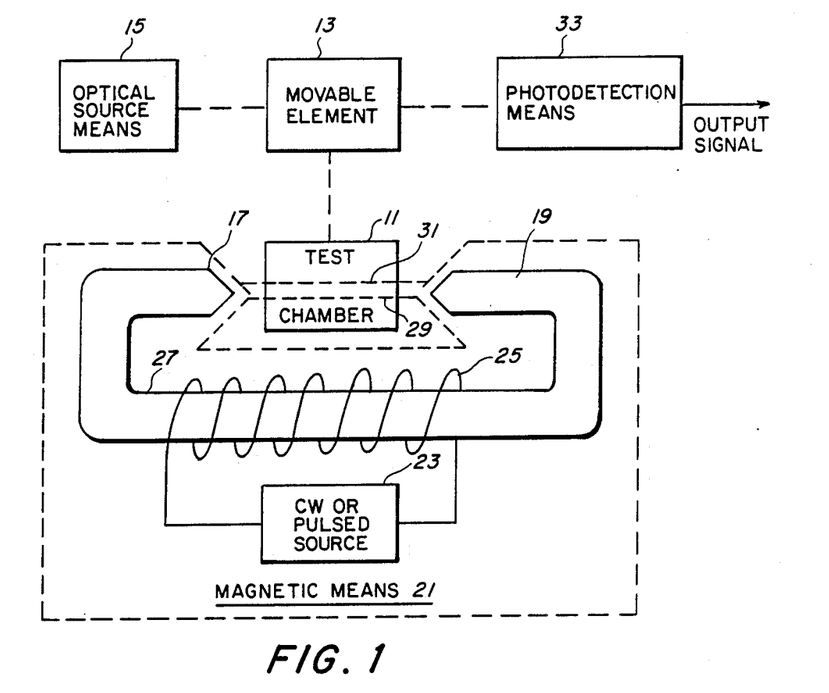
FIG. 1 is a general schematic block diagram of the invention.

Referring now to FIG. 1, a general schematic block diagram of the invention is shown. As described before, the invention is directed to an apparatus for measuring the concentration of a paramagnetic or diamagnetic gas in a gaseous mixture. A sample of this gaseous mixture to be measured is placed in a sample holder or test chamber 11 which, in turn, is coupled to a movable element 13. An optical source means 15, having a known output light intensity, directs its output light to the movable element 13. Disposed across the test chamber 11 are pole pieces 17 and 19 of magnetic means 21. Magnetic means 21 can be implemented to operate in any of three modes of operation.

As shown in FIG. 1, magnetic means 21 can comprise a CW (continuous wave) or pulsed source 23 for energizing a coil 25 wound around a core 27. The core 27 includes pole pieces 17 and 19. The source 23 provides an electrical signal at a frequency of, for example, 2 KHz. In response to this electrical signal, the coil 25 and core 27 cooperate to generate a magnetic field across the pole pieces 17 and 19 and, hence, across the test chamber 11.

When the source 23 is a CW source, a CW magnetic field will be applied continuously across the test chamber 11 during a first mode of operation. When the source 23 is a pulsed source, a magnetic field will be periodically applied across the test chamber 11 during a second mode of operation. Thus, in this second mode of operation, the source 23 could provide, for example a 5 to 20 seconds long electrical signal to the coil 25 every two minutes. As a result, in this example a magnetic field would be applied across the test chamber 11 for 5 to 20 seconds out of every two minutes.

In a third mode of operation, the source 23 and coil 25 could be removed, and the core 27 and poles 17 and 19 could comprise a permanent magnet which applies a DC magnetic field across the test chamber 11.

It should be understood that henceforth the magnetic means 21 can be implemented to operate in any of the above-described three modes of operation.

It should be noted at this time that the pole pieces 17 and 19 are designed to generate the strongest possible field gradient region or part 29 of the magnetic field across the pole pieces 17 and 19. When the gaseous mixture in the test chamber 11 is to be tested for the concentration therein of a paramagnetic gas (such as oxygen or nitric oxide gas) or a diamagnetic gas (such as nitrogen, water vapor, argon or xenon), the center line 31 of the chamber 11 is located or positioned a little above or below the strongest field gradient region 29 of the magnetic field (as shown in FIG. 1).

In operation, the application of a magnetic field across the test chamber 11 causes the magnetic dipoles of the paramagnetic/diamagnetic gas molecules to experience a torque tending to align the dipoles with or against the applied magnetic field. In the case of a paramagnetic gas, such as oxygen, unpaired electron spins tend to align with the applied field. Very quickly the population of dipole alignments shifts slightly in favor of alignment with the applied field. The force of each dipole is proportional to the local field gradient. The oxygen molecules present in the gaseous mixture in the chamber 11 are drawn toward the strongest field gradient region 29 of the magnetic field. Non-magnetic gases present in the sample gas in chamber 11 will not be affected by the magnetic field.

The attraction of the paramagnetic gas (such as oxygen) in the chamber 11 toward the region 29 will cause the movable element 13 to be displaced by a distance proportional to the concentration of the paramagnetic gas in the gaseous mixture in the chamber 11.

If, as discussed before, the gaseous mixture in the chamber 11 is to be tested for the concentration of a diamagnetic gas therein, the center line 31 of the chamber 11 is positioned a little below the strongest field gradient region 29 of the magnetic field. In this case, when a magnetic field is applied across the chamber 11, the molecules of the diamagnetic gas are repelled further away from the region 29, while the molecules of nonmagnetic gases in the mixture are unaffected by the magnetic field. This causes the movable element 13 to be displaced by a distance proportional to the concentration of the diamagnetic gas in the gaseous mixture in the chamber 11.

A photodetection means 33 is optically coupled to the movable element 13 to receive a light signal therefrom. This light signal, which is derived from the light from the optical source means 15, has a characteristic indicative of the distance that the movable element 13 was displaced by the application of a magnetic field across the test chamber 11. It will be recalled that the movable element 13 was displaced by a distance proportional to the concentration of a paramagnetic or diamagnetic gas in the gaseous mixture in the chamber 11. Therefore, the photodetection means 33 is responsive to the light signal from the movable element 13 for providing an output signal which has an amplitude proportional to the concentration of the paramagnetic or diamagnetic gas in the gaseous mixture in the chamber 11.

Seven exemplary embodiments of the invention of FIG. 1 will be respectively discussed in the following descriptions of FIGS. 2-8.

Figure 2:
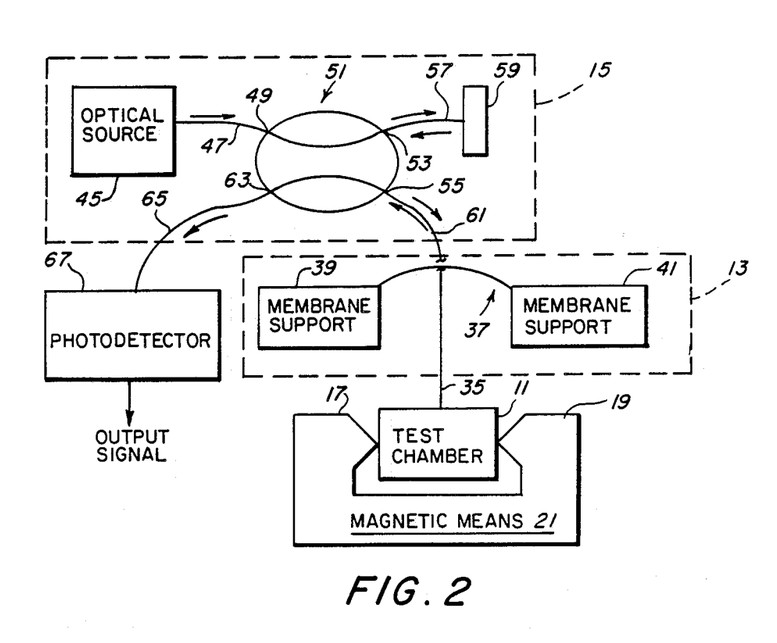
FIG. 2 is a schematic block diagram of a first embodiment of the invention.

FIG. 2 illustrates a first embodiment of the invention of FIG. 1. Essentially FIG. 2 illustrates a Michelson Interferometric paramagnetic/diamagnetic gas sensor. The sample of gas to be measured for the concentration and/or presence of paramagnetic/diamagnetic gas is placed in the test chamber 11. Test chamber 11 is then suitably suspended between pole pieces 17 and 19 of the magnetic means 21 by, for example, a non-magnetic wire 35 attached to a movable or flexible membrane 37. The flexible membrane 37 is, in turn, attached to membrane supports 39 and 41. This flexible membrane 37 has a reflective upper surface 43.

Magnetic means 21 causes a magnetic field to be applied to its pole pieces 17 and 19. As discussed before in relation to FIG. 1, this magnetic field may either be a D.C. field (in the third mode of operation when the magnetic means 21 is a permanent magnet) or an A.C. field (when the source 23 of FIG. 1 is a CW source during the first mode of operation or a pulsed source during the second mode of operation). In the case of an A.C. magnetic field of frequency $\omega$, the gas sample in the test chamber 11 will experience a force at twice the frequency of the applied field $\omega$.

Light from an optical or laser source 45 traverses an optical fiber or fiber 47 and enters a port 49 of a 3 dB coupler 51. This light is divided by the coupler 51 into two substantially equal incident light beams which are outputted from the coupler 51 at ports 53 and 55. The incident light beam from port 53 propagates through a fiber 57 to a mirror 59 and is reflected from the mirror 59 back through the fiber 57 to the port 53 as a reference light beam. The incident light beam from port 55 propagates through a fiber 61, impinges on the reflective upper surface 43 of the membrane 37, and is reflected by the surface 43 back through the fiber 61 to the port 55 as a signal light beam. Since they originated from light from the source 45 both of the reference and signal light beams are phase coherent with each other.

It will be recalled that the movement of the membrane 37, when the magnetic field is applied across the test chamber 11, is proportional to the amount or concentration of paramagnetic/diamagnetic gas present in the gaseous mixture in test chamber 11. Such movement of the membrane 37 therefore changes the distance that the incident light from fiber 61 must traverse before it is reflected by the membrane 37 back through the fiber 61 to the port 55 as the signal light beam. As a result, the phase of this light reflected back to the port 55 is changed as a function of the distance that the membrane 37 has been moved or displaced when the magnetic field is applied across the test chamber 11. Another way of saying this is that the phase relationship or phase difference between the reference light beam at port 53 and the signal light beam at port 55 is determined as a function of the distance that the membrane 37 is displaced when the magnetic field is applied across the test chamber 11. The effect of this phase difference between the phase coherent reference and signal light beams being applied to the 3 dB coupler 51 can best be explained by briefly examining the operation of a 3 dB coupler, such as the 3 dB coupler 51.

A characteristic of the 3 dB coupler 51 is that, based upon the phase difference between the reference light beam at port 53 and the signal light beam at port 55, either all of the light from the reference and signal light beams is outputted at one of the ports 49 and 63 or one portion of the reference and signal light beams is outputted at the port 49 while the remaining portion of those beams is outputted at the port 63. Another way of stating this is that the reflected reference and signal light beams recombine in the 3 dB coupler 51 and constructively or destructively interfere with each other at port 63. Thus, the intensity of the recombined light at port 63 is a function of the phase difference between the reference and signal light beams.

Recombined light at the port 63 propagates through a fiber 65 to a photodetector 67. The photodetector 67 is responsive to this recombined light for developing an electrical output signal that has an amplitude proportional to the concentration of paramagnetic/diamagnetic gas in the test chamber 11.

As indicated above, the embodiment of FIG. 2 illustrates a Michelson Interferometric paramagnetic/diamagnetic gas sensor. The Michelson Interferometer of FIG. 2 includes the 3 dB coupler 51, the fibers 47, 57, 61 and 65, the mirror 59 and the membrane 37.

Figure 3:
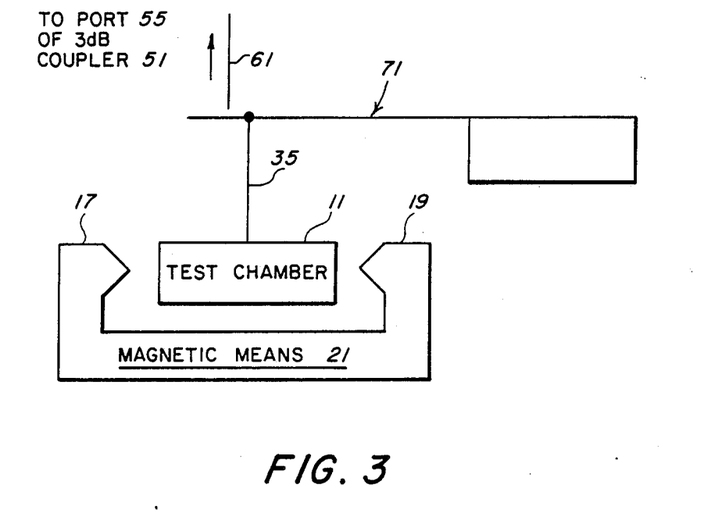
FIG. 3 is a schematic block diagram of a second embodiment of the invention.

Referring now to FIG. 3, a modification to the first embodiment of FIG. 2 is shown. This modification produces a second embodiment of the invention. In FIG. 3, a reflective cantilever 71 replaces the membrane 37 and membrane supports 39 and 41 of FIG. 2. The non-magnetic wire 35 is coupled to the cantilever 71 to support the test chamber 11 between the pole pieces 17 and 19 of the magnetic means 21. Fiber 61 is coupled to port 55 of the 3 dB coupler 51. Other than these changes, the structure and operation of the second embodiment of FIG. 3 are the same as those of the first embodiment of FIG. 2.

Figure 4:
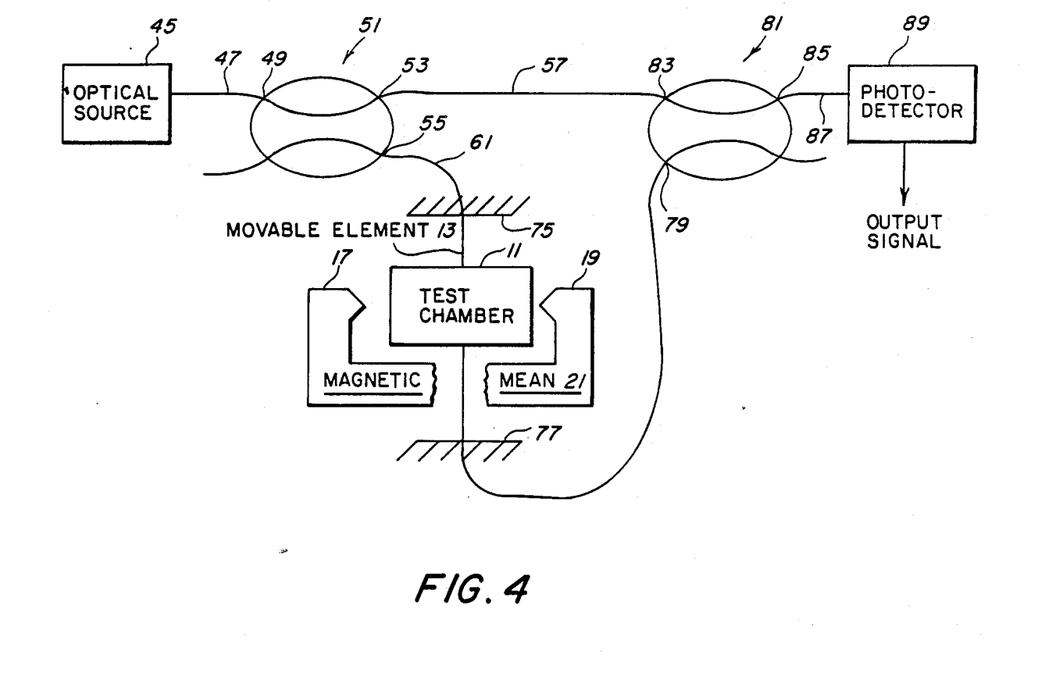
FIG. 4 is a schematic block diagram of a third embodiment of the invention.

FIG. 4 illustrates a third embodiment of the invention, namely a Mach Zehnder Interferometric paramagnetic/diamagnetic gas sensor. The embodiment of FIG. 4 differs from the embodiments of FIGS. 2 and 3 in that it uses two 3 dB couplers 51 and 81 and no mirrors or reflective surfaces, whereas each of the embodiments of FIGS. 2 and 3 uses only one 3 dB coupler 51, a mirror 59 and a reflective surface (of the membrane 43 in FIG. 2 and of a cantilever 71 in FIG. 3).

In the embodiment of FIG. 4 the test chamber 11 is attached to the fiber 61 which passes through the chamber 11. The fiber 61 is also stretched and attached to fiber supports 75 and 77. Opposite ends of the fiber 61 are respectively attached to the port 55 of the 3 dB coupler 51 and to a first input port 79 of a second 3 dB coupler 81. In this embodiment of FIG. 4, the fiber 61 represents the movable element 13 of FIG. 1.

In operation, light from the optical or laser source 45 traverses the fiber 47 and enters port 49 of the 3 dB coupler 51. This light is divided by the coupler 51 into two substantially equal light beams which are outputted from the coupler 51 at ports 53 and 55. The light beam from port 53 propagates through fiber 57 to a second input port 83 of the 3 dB coupler 81 as a reference beam. On the other hand, the light beam from port 55 propagates through fiber 61 to the first input port 79 of coupler 81 as a signal beam.

The application of a magnetic field by the magnetic means 21 to the pole pieces 17 and 19 causes the magnetic field to be applied across the test chamber 11. This magnetic field pulls the test chamber 11 in, for example, a downward direction and further stretches the fiber 61 to produce an associated phase shift in the signal beam at the first input port 79 of coupler 81. This phase shift in the signal beam is proportional to the distance that the fiber 61 is stretched when the magnetic field is applied across the test chamber 11.

The phase shifted signal beam at the port 79 and the reference beam at the port 83 are combined or mixed in the 3 dB coupler 81 to produce at an output port 85 of the coupler 81 a combined light signal having an intensity proportional to the phase difference between the signal and reference beams at the respective input ports 79 and 83. This combined light signal at output port 85 propagates through a fiber 87 to a photodetector 89. In response to the intensity of this combined light signal, the photodetector 89 produces an electrical output signal that has an amplitude proportional to the concentration of paramagnetic/diamagnetic gas in the test chamber 11.

As stated before, the embodiment of FIG. 4 illustrates a Mach Zehnder Interferometric paramagnetic/diamagnetic gas sensor. The Mach Zehnder Interferometer of FIG. 4 includes the two 3 dB couplers 51 and 81 and the fibers 47, 57, 61 and 87.

Figure 5:
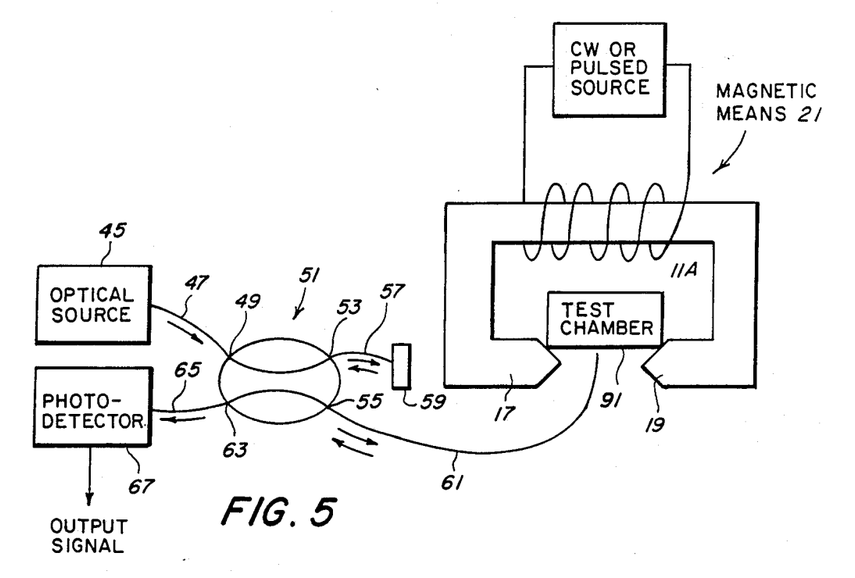
FIG. 5 is a schematic block diagram of a fourth embodiment of the invention.

Referring now to FIG. 5, a fourth embodiment of the invention of FIG. 1 is shown. Basically, FIG. 5 illustrates another modification of the embodiment of FIG. 2. In FIG. 5 a reflective movable membrane 91 is directly attached to a test chamber 11A and acts as one wall of the chamber 11A. The chamber 11A is placed between the pole pieces 17 and 19 of magnetic means 21. The wire 35, membrane 37 and membrane supports 39 and 41 of FIG. 2 are omitted from the embodiment of FIG. 5. All of the remaining elements 21, 45, 47, 51, 57, 59, 61, 65 and 67 of FIG. 5 are similar in structure and operation to the corresponding elements shown in FIG. 2 and, hence, require no further description.

The fiber 61 of the Michelson Interferometer (comprised of the 3 dB coupler 51, the fibers 47, 57, 61 and 65, the mirror 59 and the reflective movable membrane 91) senses the displacement of the membrane 91 when the magnetic field from the magnetic means 21 is applied across the test chamber 11A. As similarly discussed in relation to FIG. 2, this displacement of the membrane 91 by the application of the magnetic field across test chamber 11A produces a phase shift in the signal light beam at the port 55. The phase difference between the reference light beam at port 53 and the signal light beam at port 55 causes the 3 dB coupler 51 to produce at its output port 63 a light signal having an intensity proportional to the phase difference between these two light beams. This light signal propagates through the fiber 65 and is detected by the photodetector 67, which produces an electrical output signal that has an amplitude proportional to the concentration of paramagnetic/diamagnetic gas in the test chamber 11A.

Figure 6:
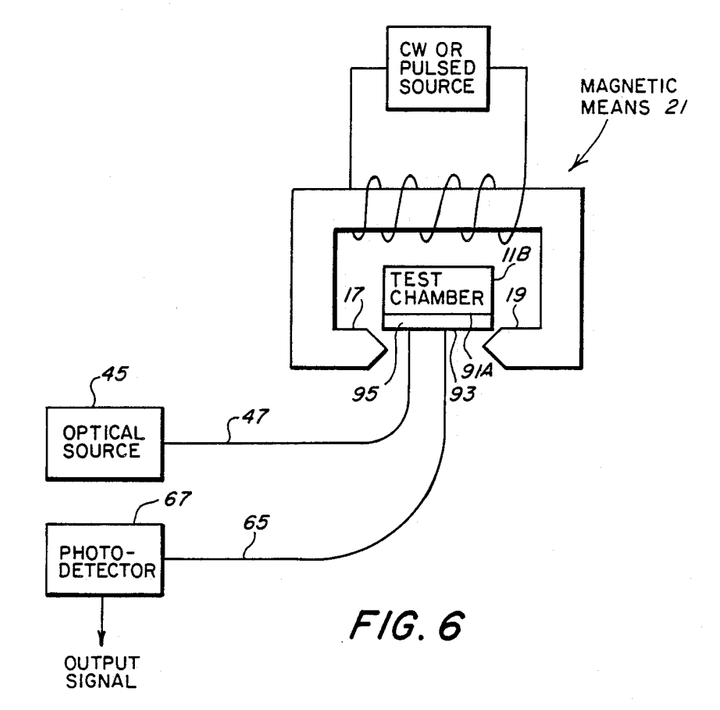
FIG. 6 is a schematic block diagram of a fifth embodiment of the invention.

FIG. 6 illustrates a fifth embodiment of the invention of FIG. 1, namely a Fabre-Perot Interferometric paramagnetic/diagmagnetic gas sensor. In this fifth embodiment the gas mixture or sample to be tested is enclosed in a test chamber 11B which has as one of its sides a reflective membrane 91A. A reflector or mirror 93 is attached to the test chamber 11B and faces the reflective membrane 91A. The membrane 91A and mirror 93 form a Fabre-Perot Interferometer, while the space between the membrane 91A and mirror 93 forms a cavity 95 of the Fabre-Perot Interferometer.

Light from optical source 45 is brought into the cavity 95 between the membrane 91A and mirror 93 by fiber 47. To enable light to pass from the fiber 47 into the cavity 95, the mirror 93 is a partially transmissive and partially reflective mirror through which part of the light from the fiber 47 passes.

The light in the cavity 95 reflects back and forth between the reflective membrane 91A and the mirror 93 until all of that light that can come out of the mirror 93 of the cavity 95 comes out of the mirror 93. Each time that light is reflected from the membrane 91A to the mirror 93, a little bit of that light leaks out of the mirror 93 and propagates through fiber 65 to photodetector 67. To enable part of the reflecting light to pass from the cavity 95 into the fiber 65, the mirror 93, as discussed before, is a partially transmissive and partially reflective mirror through which part of the light reflecting from the membrane 91A passes.

Each time that light reflects from the membrane 91A back to the mirror 93, a phase shift is introduced into the reflecting light as a function of the distance between the membrane 91A and mirror 93. All of these phase shifts of the reflecting light are cumulative and produce a composite phase shift which, in turn yields an intensity of light which is outputted from the cavity 95 to the photodetector 67 by way of fiber 65. The intensity of light that comes out of the cavity 95 is proportional to the distance between the reflective membrane 91A and the mirror 93. For example, if all the light coming out of the cavity 95 is in phase (0° or 360°) with the light that entered the cavity 95 from fiber 45, the intensity of the light being outputted through the mirror 93 of the cavity 95 is high. On the other hand, if the reflecting light is out of phase (90° or 270°) with the light that entered the cavity 95, no light will be outputted through the mirror 93 of the cavity 95. Finally, if the reflecting light is somewhere between in-phase and out-of-phase with respect to the light that entered the cavity 95, some intermediate intensity of light will be outputted from the mirror 93 of the cavity 95.

So the intensity or amount of light that comes out of the mirror 93 of the cavity 95 is proportional to the phase relationship of the output light which, in turn, is proportional to the distance between the membrane 91A and the mirror 93. A Fabre-Perot Interferometer works by sensing this distance or separation between the membrane 91A and the mirror 93.

If no magnetic field is being applied by the magnetic means 21 across the test chamber 11B, a paramagnetic gas in the test chamber 11B will not expand (or a diamagnetic gas in the test chamber 11B will not contract). In this case, the photodetector 67 will develop a reference output signal.

When a magnetic field is applied by the magnetic means 21 across the test chamber 11B, a paramagnetic gas in the chamber 11B will expand, or a diamagnetic gas in the chamber 11B will contract. Such expansion or contraction of the gas in the chamber 11B will cause the membrane 91A to according move either outward or inward as a function of the concentration of the paramagnetic/diamagnetic gas in the chamber 11B, thereby changing the distance between the membrane 91A and mirror 93. The Fabre-Perot Interferometer senses this new distance or separation between the membrane 91A and mirror 93 and outputs an intensity of light from the cavity 95 which is proportional to this new distance between the membrane 91A and mirror 93. This intensity of light is detected by the photodetector 67, which produces an electrical output signal that is proportional to the distance between the membrane 91A and mirror 93 and hence is proportional to the concentration of paramagnetic or diamagnetic gas in the gaseous mixture in the chamber 11B.

Figure 7:
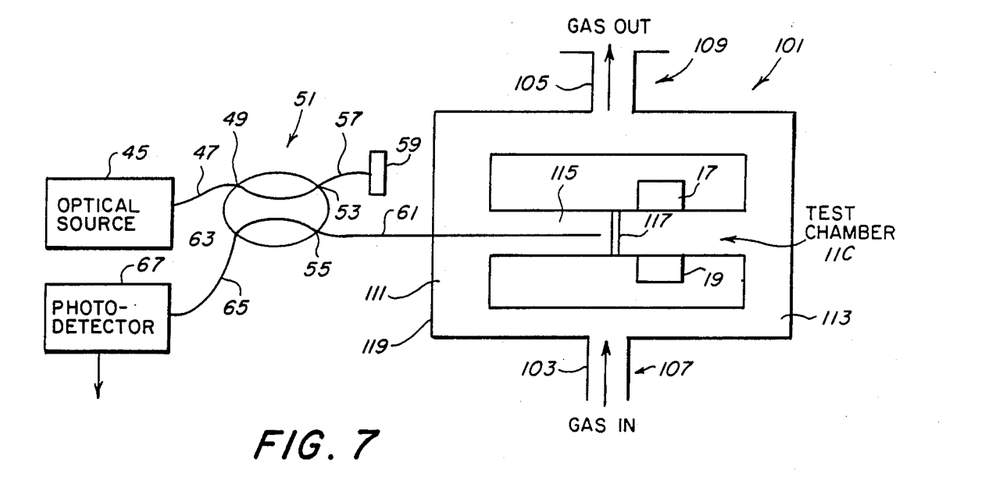
FIG. 7 is a schematic block diagram of a sixth embodiment of the invention.

Referring now to FIG. 7, a sixth embodiment of the invention of FIG. 1 is shown. This embodiment is another type of Michelson Interferometric paramagnetic/diamagnetic gas sensor.

The gas sensor of FIG. 7 includes the optical source 45, 3 dB coupler 51, fibers 47, 57, 61 and 65, mirror 59 and photodetector 67, which elements are similar in structure and operation to the corresponding elements shown in FIG. 2 and, hence require no further description. The gas sensor of FIG. 7 further includes a chamber 101 which comprises inlet and outlet ports 103 and 105 respectively disposed at lower and upper portions 107 and 109 of the chamber 101, flow tubes or channels 111 and 113 located on opposite sides of the chamber 101 and extending between the inlet and outlet ports 103 and 105, a connecting tube or cross passage 115 coupled between the channels 111 and 113, and a reflective membrane 117 disposed across the length of the cross passage 115 between the channels 111 and 113. That portion of the cross passage 115 bounded by the membrane 117, pole pieces 17 and 19 and channel 113 operates as a test chamber 11C. The free end of the fiber 61 is passed into the cross passage 115 by means of, for example, a hole (not shown) in a sidewall 119 of the chamber 101. The fiber 61 (of the Michelson Interferometer) is used to sense the position of the reflective membrane 117.

In operation, a gas is flowed into the inlet port 103 and goes equally into both of the channels 111 and 113 and into both sides of the cross passage 115 before exiting from outlet port 105. A magnetic field is applied to pole pieces 17 and 19 of a magnetic means 21 (FIG. 2). If a diamagnetic gas is present in the flowing gas, the magnetic field will cause excess gas to leave the cross passage 115 which, in turn, causes a pressure imbalance that deflects the membrane 117 toward the fiber 61. If a paramagnetic gas is present in the flowing gas, the magnetic field will cause excess gas to enter the cross passage 115 which, in turn, causes a pressure imbalance that deflects the membrane 117 away from the fiber 61. The distance that the membrane 117 is deflected is proportional to the concentration of the paramagnetic or diamagnetic gas in the gas flowing through the chamber 101. The deflection of the membrane 117 is detected by the photodetector 67 by way of the fibers 61 and 65 and their connecting Michelson Interferometer, as discussed in relation to FIG. 2. Thus, the photodetector 67 develops an electrical output signal which has an amplitude proportional to the concentration of paramagnetic or diamagnetic gas flowing through the chamber 101.

Different types of interferometers have been used in the various interferometric paramagnetic/diamagnetic gas sensors described in the embodiments of FIGS. 2-7. However, all of these interferometric gas sensors of FIGS. 2-7 work on the same principle, namely, the application of a magnetic field to a gaseous mixture containing a paramagnetic/diamagnetic gas produces a deflection of a movable element which causes a change in the phase difference between a reference light and a signal light. That phase difference is optically sensed by an interferometer and photodetected to provide an electrical output signal having an amplitude proportional to the concentration of the paramagnetic/diamagnetic gas in the gaseous mixture.

It should be noted at this time that optical interferometers, as used in the above-described gas sensors of FIGS. 2-7, are the most sensitive ways to measure a very small displacement of the above-described movable element. More specifically, the interferometric paramagnetic/diamagnetic gas sensors of FIGS. 2-7 can measure a movable element displacement on the order of a fraction of one angstrom and, therefore, are much more sensitive than conventional gas sensors, which rely on less sensitive detection schemes.

Figure 8:
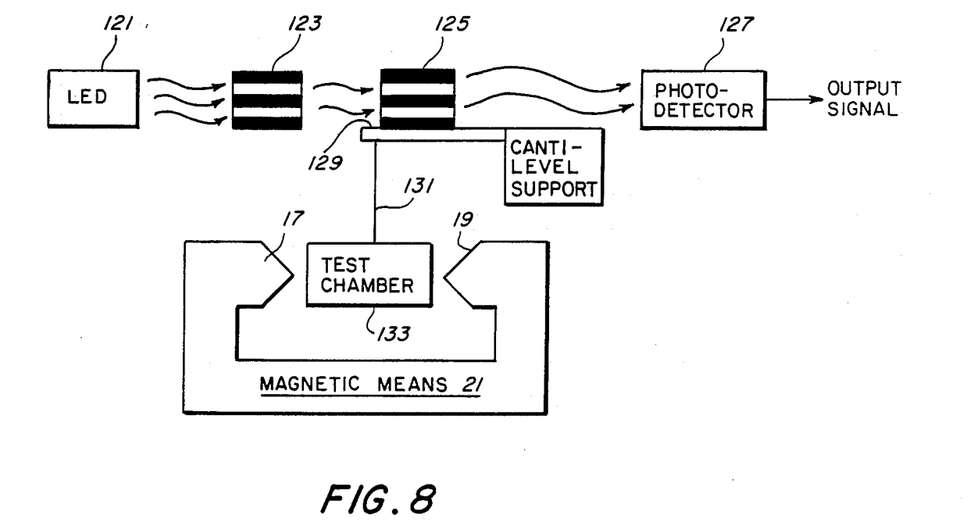
FIG. 8 is a schematic block diagram of a seventh embodiment of the invention.

Referring now to FIG. 8, a seventh embodiment of the invention of FIG. 1 is illustrated. Whereas the embodiments of FIGS. 2-7 deal with various types of interferometric paramagnetic/diamagnetic gas sensors, FIG. 8 is directed to an amplitude mode paramagnetic/-diamagnetic gas sensor.

In the amplitude mode of gas sensor of FIG. 8, a light emitting diode (LED) 121 shines a light beam through two horizontally aligned masks or gratings 123 and 125 to a photodetector 127. Grating 125 is attached to the upper part of a cantilever beam 129 and is movable relative to the grating 123 which is fixed in position. A non-magnetic wire 131 is coupled to the cantilever beam 129 to support a test chamber 133 between pole pieces 17 and 19 of magnetic means 21. The test chamber 133 contains a sample of a gaseous mixture to be measured for the concentration of a paramagnetic or diagmagnetic gas in the gaseous mixture.

When no magnetic field is applied to the pole pieces 17 and 19 by the magnetic means 21, the gratings 123 and 125 are horizontally aligned with each other to allow a maximum amount of light from LED 121 to reach the photodetector 127. In this case the photodetector 127 converts that light to an electrical output signal to establish a reference level.

The application of a magnetic field to the pole pieces 17 and 19 by the magnetic means 21 causes the magnetic field to be applied across the test chamber 133. This magnetic field pulls the test chamber 133 in, for example, a downward direction, moving the grating 125 out of alignment with the grating 123 by a distance proportional to the concentration of paramagnetic/diamagnetic gas in the test chamber 133, As a result, this movement of the grating 125 modulates the transmission of light from the LED 121 to the photodetector. Thus, the intensity or amount of light received by the photodetector 127 is decreased by an amount proportional to the concentration of paramagnetic or diamagnetic gas in the test chamber 133. The photodetector 127 is responsive to this lower intensity of light for developing an electrical output signal which is proportional to the concentration of paramagnetic or diamagnetic gas in the test chamber 133.

Each of the embodiments of FIGS. 2-8 can use either a CW magnetic field or a pulsed magnetic field, or even a DC magnetic field, depending on the type of measurement to be made. Either a relative measurement or an absolute measurement can be made in regard to the concentration of paramagnetic or diamagnetic gas in the gaseous mixture in the associated test chamber. A relative measurement just indicates whether the concentration of paramagnetic or diamagnetic gas in the gaseous mixture has increased or decreased. Thus, it is a measurement of the relative change in the percent of the paramagnetic or diamagnetic gas in the gaseous mixture being tested. On the other hand, an absolute measurement is a measurement of the percent or concentration of paramagnetic or diamagnetic gas in the gaseous mixture being tested.

When only a relative measurement is needed, a CW or DC magnetic field is applied to the associated test chamber holding the gaseous mixture to be tested. In this case the concentration of the paramagnetic/diamagnetic gas is measured at a first time. Then later on a different gas sample is put in the associated test chamber of FIGS. 2-6 and 8, or a different gas sample is flowed into the test chamber of FIG. 7. Then a second measurement is made to determine the relative change in the percent of paramagnetic or diamagnetic gas in the gaseous mixture being tested.

When an absolute measurement is needed, a reference level must first be established at the output of the associated photodetector. To obtain an absolute measurement in the embodiments of FIGS. 2-8, the magnetic field is pulsed. When the magnetic field is off, a measurement is made to establish a reference level at the output of the associated photodetector. When the magnetic field is on, another measurement is made to establish a signal level (at the output of the associated photodetector) which is proportional to the concentration of the paramagnetic/diamagnetic gas in the gaseous sample being tested. The difference between the reference and signal levels will give an absolute value indicative of the percent or concentration of the paramagnetic/diamagnetic gas in the gaseous sample between tested.

To determine the absolute value of the embodiment of FIG. 7 with a CW or DC magnetic field being applied, a non-paramagnetic/diamagnetic gas is flowed into the test chamber 11A to establish a reference level. In an alternative manner, if the concentration of, for example, oxygen (a paramagnetic gas) is to be tested in a gaseous mixture, pure oxygen is flowed into the chamber 101 and test chamber 11C before a first measurement is made to establish a reference level for pure oxygen at the output of the photodetector 67. After a reference level is determined, the gaseous mixture to be tested is flowed into the chamber 101 and test chamber 11C for a time sufficient for it to completely integrate or fill the chamber 101. A second measurement is then made to establish a signal level. As stated above, the difference between the reference and signal levels will give an absolute value indicative of the percent or concentration of the paramagnetic/diamagnetic gas in the gaseous sample being tested.

For an accurate relative or absolute measurement, the output intensity of light from the optical source (laser or LED), as well as the specific paramgnetic or diamagnetic gas being tested for, must be known.

As stated before, the use of the optical interferometric paramagnetic/diamagnetic gas sensors, as described in the embodiments of FIGS. 2–7 permits a more sensitive gas measurement because optical interferometric techniques represent the most sensitive means to measure small displacements used to sense the presence of paramagnetic or diamagnetic gases. The gas sensors of FIGS. 2–7 also can be used in explosive environments since they are totally passive and can afford remote location of the interferometer, light source and photodetector because optical fibers pass the light signals of interest over a desired distance. In addition, the gas sensors of FIGS. 2–7, as well as the gas sensor of FIG. 8, are totally immune to electromagnetic interference (EMI) and can be used in high EMI environments, like near electrically noisy machinery where conventional gas sensors cannot be used.

Therefore, what has been described is an apparatus for measuring the concentration of a paramagnetic or diamagnetic gas in a gaseous mixture to be tested by optically measuring the displacement of a movable element when a magnetic field is applied to the gaseous mixture.

It should therefore readily be understood that many modifications and variations of the present invention are possible within the purview of the claimed invention. It is therefore to be understood that within the scope of the appended claims, the invention may be practiced otherwise than as specifically described.

What is claimed and desired to be secured by Letters Patent of the United States is:

1. An apparatus for measuring the concentration of a paramagnetic or diamagnetic gas in a gaseous mixture, said apparatus comprising:
   a chamber adapted to contain a gaseous mixture to be measured for the amount of a paramagnetic or diamagnetic gas in said mixture;
   a reflective movable element coupled to said chamber;
   a reflector;
   optical source means for providing light to said movable element, said optical source means including:
      an optical source for producing an input beam;
      an optical coupler having first and second input ports and first and second output ports, said optical coupler being responsive to the application of said input beam to said first input port for providing substantially equal first and second incident beams at said first and second output ports, respectively;
      a first light path for passing said first incident beam to said movable element for reflection therefrom and for passing said reflected first incident beam to said first output port with a phase indicative of the distance that said movable element is displaced;
      a second light path for passing said second incident beam to said reflector for reflection therefrom and for passing said reflected second incident beam to said second output port with a reference phase, said optical coupler being responsive to said reflected first and second incident beams for developing at said second input port a light signal having an intensity proportional to the phase relationship between said reflected first and second incident beams;
   magnetic means for developing a magnetic field across said chamber, said paramagnetic or diamagnetic gas in said chamber being responsive to the application of said magnetic field across said chamber for causing said movable element to be displaced by a distance proportional to the concentration of said paramagnetic or diamagnetic gas in said mixture; and
   photodetection means for receiving a light signal from said movable element, said light signal having a characteristic indicative of the distance that said movable element is displaced, said photodetection means being responsive to said light signal for providing an output signal having an amplitude proportional to the concentration of said paramagnetic or diamagnetic gas in said gaseous mixture, said photodetection means including a photodetector responsive to said light signal for developing an electrical signal that has an amplitude proportional to the concentration of paramagnetic or diamagnetic gas in said gaseous mixture.

2. The apparatus of claim 1 wherein said magnetic means includes:
   a pair of pole pieces separated by a gap for developing a magnetic field across said gap, said chamber being disposed within said gap.

3. The apparatus of claim 2 wherein;
   said magnetic means includes means for causing said magnetic means to generate a periodically excited magnetic field.

4. The apparatus of claim 1 wherein:
   each of said first and second light paths is an optical fiber.

5. The apparatus of claim 1 wherein:
   said optical source is a laser.

6. The apparatus of claim 1 further including:
   first and second supports for supporting said movable element; and
   means coupled between said movable element and said chamber for suspending said chamber in said magnetic field.

7. The apparatus of claim 6 wherein:
   said movable element is a reflective membrane;
   said reflector is a mirror; and
   said optical coupler is a 3 dB coupler.

8. The apparatus of claim 7 wherein said magnetic means includes:
   a pair of pole pieces separated by a gap for developing a magnetic field across said gap, said chamber being disposed within said gap.

9. The apparatus of claim 7 wherein:

said magnetic means includes means for causing said magnetic means to generate a periodically excited magnetic field.

10. The apparatus of claim 1 further including:
a support for holding said movable element at a first portion of said movable element; and
means coupled to a second portion of said movable element for suspending said chamber in said magnetic field.

11. The apparatus of claim 10 wherein:
said movable element is a reflective cantilever beam to which said chamber is coupled by means of said suspending means at said second portion;
said reflector is a mirror; and
said optical coupler is a 3 dB coupler.

12. The apparatus of claim 10 wherein said magnetic means includes:
a pair of pole pieces separated by a gap for developing a magnetic field across said gap, said chamber being disposed within said gap.

13. The apparatus of claim 10 wherein:
said magnetic means includes means for causing said magnetic means to generate a periodically excited magnetic field.

14. The apparatus of claim 1 wherein:
said movable element is attached to said chamber and acts as one wall of said chamber.

15. The apparatus of claim 14 wherein:
said movable element is a reflective membrane;
said reflector is a mirror; and
said optical coupler is a 3 dB coupler.

16. The apparatus of claim 14 wherein said magnetic means a pair of pole pieces separated by a gap for developing a magnetic field across said gap, said chamber being disposed within said gap.

17. The apparatus of claim 14 wherein:
said magnetic means includes means for causing said magnetic means to generate a periodically excited magnetic field.

18. An apparatus for measuring the concentration of a paramagnetic or diamagnetic gas in a gaseous mixture, said apparatus comprising:
a chamber adapted to contain a gaseous mixture to be measured for the amount of a paramagnetic or diamagnetic gas in said mixture;
a movable element coupled to said chamber;
optical source means for providing light to said movable element;
magnetic means for developing a magnetic field across said chamber, said paramagnetic or diamagnetic gas in said chamber being responsive to the application of said magnetic field across said chamber for causing said movable element to be displaced by a distance proportional to the concentration of said paramagnetic or diamagnetic gas in said mixture; and
photodetection means for receiving a light signal from said movable element, said light signal having a characteristic indicative of the distance that said movable element is displaced, said photodetection means being responsive to said light signal for providing an output signal having an amplitude proportional to the concentration of said paramagnetic or diamagnetic gas in said gaseous mixture, said photodetection means including:
a first 3 dB coupler having first and second input ports and first and second output ports; and
a photodetector coupled to said first output port;

said optical source means including:
an optical source for producing an input beam;
a second 3 dB coupler having third and fourth input ports and third and fourth output ports, said second 3 dB coupler being responsive to the application of said input beam to said third input port for providing substantially equal first and second incident beams at said third and fourth output ports, respectively;
first and second supports spaced apart between said first and second 3 dB couplers;
a first fiber coupled between said third output port and said first input port for passing said first incident beam to said first input port with a reference phase; and
a second fiber coupled between said fourth output port and said second input port for passing said second incident beam to said second input port, an intermediate portion of said second fiber being stretched between said first and second supports, said intermediate portion being said movable element, said intermediate portion passing through said chamber to support said chamber in said magnetic field;
said paramagnetic gas being responsive to the application of said magnetic field across said chamber for displacing said chamber and stretching said intermediate portion to produce an associated phase shift in the second incident beam at said second input port, said associated phase shift being indicative of the distance that said movable element is displaced, said first 3 dB coupler developing at said first output port a light signal having an intensity proportional to the phase difference between said first and second incident beams at said first and second input ports, said photodetector being responsive to said light signal for providing said output signal.

19. The apparatus of claim 18 wherein said magnetic means includes:
a pair of pole pieces separated by a gap for developing a magnetic field across said gap, said chamber being disposed within said gap.

20. The apparatus of claim 18 wherein:
said magnetic means includes means for causing said magnetic means to generate a periodically excited magnetic field.

21. An apparatus for measuring the concentration of a paramagnetic or diamagnetic gas in a gaseous mixture, said apparatus comprising:
a chamber adapted to contain a gaseous mixture to be measured for the amount of a paramagnetic or diamagnetic gas in said mixture;
a movable element coupled to said chamber, said movable element being a reflective membrane attached to said chamber and forming one of its sides;
optical source means for providing light to said reflective membrane;
a reflector attached to said chamber and disposed from and facing said reflective membrane, said reflector being adapted to allow light from said optical source means to pass therethrough to said reflective membrane, said light reflecting back and forth between said reflective membrane and said reflector, said reflector being further adapted to allow a portion of said reflecting light to exit therethrough as a function of the distance between said reflective membrane and said reflector;

magnetic means for developing a magnetic field across said chamber, said paramagnetic or diamagnetic gas in said chamber being responsive to the application of said magnetic field across said chamber for causing said reflective membrane to be displaced from said reflector by a distance proportional to the concentration of paramagnetic or diamagnetic gas in said mixture; and photodetection means for receiving a light signal from said reflective membrane, said light signal having a characteristic indicative of the distance that said movable element is displaced, said photodetection means being coupled to said reflector for receiving said portion of said reflecting light exiting said reflector, said photodetection means being responsive to said portion for developing said output signal having an amplitude proportional to the concentration of said paramagnetic or diamagnetic gas in said gaseous mixture.

22. The apparatus of claim 21 further including first and second optical fibers each having first and second ends, and wherein:

said reflector has first and second apertures for respectively receiving said first ends of said first and second optical fibers;

said optical source means is coupled to said second end of said first optical fiber for transmitting light to said reflective membrane; and said photodetection means is coupled to said second end of said second optical fiber for receiving said portion passing through said second optical fiber.

23. The apparatus of claim 21 wherein said magnetic means includes:

a pair of pole pieces separated by a gap for developing a magnetic field across said gap, said chamber being disposed within said gap.

24. The apparatus of claim 21 wherein:

said magnetic means includes means for causing said magnetic means to generate a periodically excited magnetic field.

25. An apparatus for measured the concentration of a paramagnetic or diamagnetic gas in a gaseous mixture, said apparatus comprising:

a chamber adapted to contain a gaseous mixture to be measured for the amount or a paramagnetic or diamagnetic gas in said mixture, said chamber including first and second channels and a cross channel extending between said first and second channels, said cross channel having a central portion;

a movable element coupled to said chamber, said movable element being coupled across said central portion, said movable element having a first reflective side and a second side;

optical source means for providing light to said movable element, said optical source means including:
an optical source for producing an input beam;
an optical coupler having first and second input ports and first and second output ports, said optical coupler being responsive to the application of said input beam to said first input port for providing substantially equal first and second incident beams at said first and second output ports, respectively;
a reflective element; and
a first optical fiber for passing said first incident beam to said reflective element for reflection therefrom as a first reflected beam and for passing said first reflected beam to said first output port with a reference phase;

magnetic means for developing a magnetic field across said chamber, said paramagnetic or diamagnetic gas in said chamber being responsive to the application of said magnetic field across said chamber for causing said movable element to be displaced by a distance proportional to the concentration of said paramagnetic or diamagnetic gas in said mixture;

photodetection means for receiving a light signal from said movable element, said light signal having a characteristic indicative of the distance that said movable element is displaced, said photodetection means being responsive to said light signal for providing an output signal having an amplitude proportional to the concentration of said paramagnetic or diamagnetic gas in said gaseous mixture;

inlet and outlet means coupled to said chamber for introducing into said first, second and cross channels a flowing non-paramagnetic/diamagnetic gas during a first mode of operation and a flowing gaseous mixture containing a paramagnetic or diamagnetic gas during a second mode of operation; and a second optical fiber coupled between said first reflective side of said movable element and said second output port;

said magnetic means applying said magnetic field across that portion of said cross channel on said second side of said movable element, only said paramagnetic/diamagnetic gas in said flowing gaseous mixture during said second mode of operation being responsive to said magnetic field for causing said movable element to be displaced by a distance proportion to the concentration of paramagnetic/diamagnetic gas in said gaseous mixture; said second optical fiber passing said second incident beam to said first reflective side of said movable element for reflection therefrom as a second reflected beam and passing said second reflected beam to said second output port with a signal phase proportional to the distance that said movable element is displaced, said optical coupler being responsive to said first and second reflective beams for developing at said second input port an optical signal having an intensity proportional to the phase relationship between said first and second reflected beams; and said photodetection means including a photodetector responsive to said optical signal for providing said output signal.

26. The apparatus of claim 25 wherein said magnetic means includes:

a pair of pole pieces separated by said cross channel for developing a magnetic field across said cross channel.

27. An apparatus for measuring the concentration of a paramagnetic or diamagnetic gas in a gaseous mixture, said apparatus comprising:

a chamber adapted to contain a gaseous mixture to be measured for the amount of a paramagnetic or diamagnetic gas in said mixture;

a movable element coupled to said chamber;

optical source means for providing light to said movable element;

magnetic means for developing a magnetic field across said chamber, said paramagnetic or diamagnetic gas in said chamber being responsive to the application of said magnetic field across said chamber for causing said movable element to be displaced by a distance proportional to the concentrating of said paramagnetic or diamagnetic gas in said mixture; and photodetection means for receiving a light signal from said movable element, said light signal having a characteristic indicative of the distance that said movable element is displaced, said photodetection means being responsive to said light signal for providing an output signal having an amplitude proportional to the concentration of said paramagnetic or diamagnetic gas in said gaseous mixture; and wherein:

said movable element is disposed between said optical source means and said photodetection means for controlling the amount of light passing from said optical source means to said photodetection means as a function of the distance that said movable element is displaced by the application of said magnetic field across said gaseous mixture in said chamber;

said optical source means includes:
 a light emitting diode; and
 a first mask for passing a portion of the light emitted from said diode to said movable element; and said movable element is a second mask which is movable relative to the position of said first mask for controlling the amount of light that is passed therethrough as a function of its displaced distance.

28. The apparatus of claim 27 further including:
a support for holding said second mask at a first position on said support; and means coupled to a second position on said support for suspending said chamber in said magnetic field.

29. The apparatus of claim 28 wherein:
said support is a cantilever beam having a movable portion to which said second mask and said chamber are coupled.

* * * * *